United States Patent
Furnish

(10) Patent No.: US 6,873,868 B2
(45) Date of Patent: Mar. 29, 2005

(54) MULTI-FIBER CATHETER PROBE ARRANGEMENT FOR TISSUE ANALYSIS OR TREATMENT

(75) Inventor: Simon M. Furnish, New York, NY (US)

(73) Assignee: InfraReDx, Inc., Cambridge, MA (US)

( * ) Notice: Subject to any disclaimer, the term of this patent is extended or adjusted under 35 U.S.C. 154(b) by 384 days.

(21) Appl. No.: 10/037,307

(22) Filed: Dec. 31, 2001

(65) Prior Publication Data

US 2003/0125719 A1 Jul. 3, 2003

(51) Int. Cl.$^7$ ................................................. A61B 6/00
(52) U.S. Cl. ..................................... 600/435; 600/478
(58) Field of Search ................................. 600/407–472; 604/254, 524, 525, 529, 20, 22; 606/15, 17, 18; 607/88, 89, 1; 128/898, 916

(56) References Cited

U.S. PATENT DOCUMENTS

| | | | |
|---|---|---|---|
| 3,847,483 A | | 11/1974 | Shaw et al. |
| 4,672,961 A | * | 6/1987 | Davies .......................... 606/7 |
| 4,832,023 A | * | 5/1989 | Murphy-Chutorian et al. . 606/7 |
| 4,850,351 A | * | 7/1989 | Herman et al. ................ 606/7 |
| 4,917,097 A | * | 4/1990 | Proudian et al. ............. 600/463 |
| 4,950,266 A | * | 8/1990 | Sinofsky ........................ 606/2 |
| 4,967,745 A | * | 11/1990 | Hayes et al. .................... 606/7 |
| 5,081,993 A | * | 1/1992 | Kitney et al. ............... 600/455 |
| 5,242,438 A | * | 9/1993 | Saadatmanesh et al. ...... 606/15 |
| 5,405,318 A | * | 4/1995 | Nita ............................. 604/22 |
| 5,456,259 A | * | 10/1995 | Barlow et al. ............... 600/459 |
| 5,465,726 A | * | 11/1995 | Dickinson et al. .......... 600/466 |
| 5,470,330 A | * | 11/1995 | Goldenberg et al. ............ 606/7 |
| 5,693,043 A | | 12/1997 | Kittrell et al. |
| 5,700,243 A | * | 12/1997 | Narciso, Jr. ............ 604/102.01 |
| 5,716,320 A | * | 2/1998 | Buttermore ................. 600/104 |
| 5,730,700 A | | 3/1998 | Walther et al. |
| 5,827,267 A | * | 10/1998 | Savage et al. ................ 606/16 |
| 5,830,209 A | * | 11/1998 | Savage et al. ................ 606/15 |
| 5,876,345 A | * | 3/1999 | Eaton et al. ................. 600/466 |
| 5,953,477 A | * | 9/1999 | Wach et al. ................. 385/115 |
| 6,026,316 A | * | 2/2000 | Kucharczyk et al. ........ 600/420 |
| 6,156,029 A | * | 12/2000 | Mueller ......................... 606/7 |
| 6,270,492 B1 | * | 8/2001 | Sinofsky ..................... 606/15 |
| 6,283,921 B1 | * | 9/2001 | Nix et al. ................... 600/466 |
| 6,321,106 B1 | * | 11/2001 | Lemelson ................... 600/407 |
| 6,416,234 B1 | * | 7/2002 | Wach et al. .................. 385/70 |
| 6,511,475 B1 | * | 1/2003 | Altshuler et al. .............. 606/9 |
| 6,564,088 B1 | | 5/2003 | Soller et al. |
| 2002/0183623 A1 | * | 12/2002 | Tang et al. ................. 600/476 |
| 2003/0100824 A1 | * | 5/2003 | Warren et al. .............. 600/407 |

\* cited by examiner

*Primary Examiner*—Ali Imam
(74) *Attorney, Agent, or Firm*—Fish & Richardson P.C.

(57) ABSTRACT

A catheter tip apparatus is arranged in a catheter for the delivery and collection of an energy signal to permit analysis and/or treatment of body tissue by the energy signal. The apparatus comprises an elongated housing having a plurality of annularly disposed elongated grooves arranged thereon; and a flexible energy-bearing fiber arranged in each of the elongated grooves. Each of the fibers have a proximal end in communication with an energy delivery source or a signal analysis center. Each of the fibers also have a distalmost end in communication with a reflector for analysis and treatment of body tissue in which the catheter is disposed.

43 Claims, 8 Drawing Sheets

MULTI-FIBER CATHETER PROBE ARRANGEMENT FOR TISSUE ANALYSIS OR TREATMENT

This invention relates to photo-medical devices, and more particularly to photo-medical devices that deliver and collect radiant energy to permit body tissue analysis and/or treatment, and is co-pending with commonly assigned U.S. patent application Ser No. 10/037,307 filed on Dec. 31, 2001, entitled "Catheter Probe Arrangement for Tissue Analysis by Radiant Energy Delivery and Radiant Energy Collection" which is incorporated herein by reference in its entirety.

BACKGROUND OF THE INVENTION

Field of the Invention

Prior Art

The sensing and treating of various tissue characteristics in the in vivo intravascular environment is desirous for many reasons yet difficult because it is a very harsh environment in which to conduct such analysis or treatment. The presence of blood and its constituents such as cholesterol may effect scattering and absorption of energy signals transmitted within an organ. Diagnosis and treatment of various tissues within the human body using an in vivo probe necessitates adaptive characteristics for that probe when it is inserted into a mammalian body organ.

It is an object of the present invention to provide a probe for insertion within a mammalian body which overcomes the disadvantages of the prior art.

It is a further object of the present invention to provide a minimally invasive device for wave energy transmitting (i.e. photonic) diagnosis and treatment of mammalian tissue through the use of endoscopes, catheters and other minimally invasive devices.

It is still yet a further object of the present invention to provide optical probe tip arrangement which facilitates optimum delivery and retrieval of energy signals within the human body tissue.

It is a further object of the present invention to provide a catheter probe arrangement having a plurality of signal delivery and collection fibers which are adaptable dimensionally and angularly with respect to the body tissue being analyzed and/or treated.

BRIEF SUMMARY OF THE INVENTION

The present invention provides a catheter probe apparatus and method of use of a catheter probe apparatus to analyze body tissue using a component of the energy spectrum for analysis which energy is distributed and received by an elongated multi fiber probe introduceable through a catheter into that body tissue. Such introduction of a body probe may be done through an endoscope, or other catheter-like devices for energy diagnosis and treatment of that tissue.

The probe of the present invention comprises an elongated generally cylindrically shaped housing having a first or distal and a second or proximal end. The housing in a first preferred embodiment has a central bore therethrough, which may be characterized as a lumen for receiving other elongated devices such as a guidewire or signal carrying fibers. The housing has an outer peripheral surface having a plurality of spaced apart, parallel, longitudinally directed alignment grooves thereon. A step-like ledge or shoulder may be arranged transversely with respect to the longitudinal axis of the alignment grooves to act as an abutment or stop for each flexible signal fiber disposed within the respective alignment grooves.

An enlarged generally radially directed flange is disposed at the distal most end of the alignment grooves, on the distalmost end of the probe housing. The flange may have a reflective surface thereon for directing light energy rays carried by the signal carrying fibers, as will be disclosed hereinbelow. It is contemplated that there may be from eight to twelve or more alignment grooves spaced about the periphery of the housing of the probe of the present invention. The ledges or shoulders arranged within the trough of the alignment grooves may be aligned in common radial plane or aligned in a number of parallel spaced apart radially directed planes with respect to the longitudinal axis of the housing. The ledges or shoulders may be of varying radial distances in height and angled so as to effect radial displacement of the fiber tips from the radialy inner surface of the respective angular groove in which it is disposed.

A further embodiment of the housing comprising the elongated probe includes a central bore or lumen through which a signal delivery fiber may be longitudinally adjustably disposed. The delivery fiber would preferably have a polished conical tip on its distalmost end. The elongated housing in this embodiment would have the plurality of parallel longitudinally directed alignment grooves spaced apart about its periphery, each of the alignment grooves having a longitudinally adjustable return fiber disposed therein. Each of the return fibers would have a polished distal face arranged at an angle with respect to its own longitudinal axis. The polished face would function as a reflective surface for incoming light energy rays to be reflected in a return path longitudinally within the return fibers. The probe or elongated housing would be longitudinally displaceable within an outermost catheter sheath.

A further embodiment is contemplated with a generally cylindrically shaped housing having a central bore which functions as a lumen for a guide wire or further light energy bearing fiber. The outer surface of the elongated probe has the aforementioned plurality of elongated alignment channels or grooves fabricated therein, with each of the elongated grooves having a flexible, light carrying fiber therein. Alternating circumferentially arranged fibers in this embodiment may comprise a delivery fiber and a return signal fiber. The delivery signal fiber and the return signal fibers may each have a polished face on its distalmost end thereon, each face disposed at an angle of about 45 degrees with respect to its longitudinal axis thereof. It is further contemplated that each individual deliver or return signal fiber may be longitudinally displaceable within their respective alignment grooves for adjustment of the desired analysis and/or treatment to mammalian body tissue being treated.

Another further embodiment of the present invention contemplates the elongated generally cylindrically shaped probe having a proximal portion of reduced diameter, a central portion having a plurality of generally parallel spaced apart alignment grooves arranged peripherally therearound, and a distalmost nose portion. The distalmost nose portion preferably has a tapered forward end and a tapered rearward edge. The tapered rearward edge, of angular configuration, is a reflective surface. An arrangement of light-signal carrying fibers would be arranged within each of the alignment grooves. The signal fibers would have a distalmost face end through which light signals would be delivered and/or received by bouncing off of the reflective angular surface on the tapered rearward edge of the nose portion of the elongated housing. The nose cone of the elongated housing distal of the alignment grooves, may also be longitudinally displaceable with respect to the longitudinal axis of the elongated housing. A reflective surface may be somewhat arcuate or segmented in cross section or have angled reflective portions thereon to effect angular displacement of light energy signals being delivered or received from tissue adjacent to the elongated probe in the distal end of a catheter in which the tissue analysis/treatment is being undertaken.

A yet further embodiment of the present invention contemplates an elongated generally cylindrically shaped housing having a proximalmost end of reduced diameter. A central bore extends through the elongated housing and out the distalmost end thereof. The distalmost half portion of the elongated housing has a plurality of generally parallel, spaced apart circumferentially disposed alignment grooves fabricated therein. The alignment grooves are parallel with respect to the longitudinal axis of the elongated housing. In this embodiment, the axial length of their respective alignment grooves are dissimilar. There is a longitudinal separation between the reflective distalmost ends of alternating alignment grooves to permit a spread in the collection and/or delivery of energy with respect to the light signal carrying fibers disposed therewithin. The distalmost end of each alignment groove in the elongated housing of this embodiment has an angled mirror face therein. The arcuate segment defining the mirror face for each alignment groove is preferably arcuately (circumferentially) larger than the arcuate (circumferential) width of each respective alignment groove. Such longitudinal displacement between adjacent light signal carrying fibers permits greater light dispersal and light gathering (collection) paths of analyses of tissue being examined or treated.

Another embodiment which is generally similar to the aforementioned embodiment, contemplates mirrors on the distal end of the alignment grooves being the same arcuate dimension as the respective alignment grooves in which they sit.

Yet another embodiment contemplated for the elongated probe in the distal end of a catheter may comprise a single elongated extrusion having a bore therethrough, the extrusion's distal end defining the probe component in this example. The probe in this component also includes a plurality of axially aligned alignment grooves exterior to the extrusion, the alignment grooves each carrying a fiber spaced therewithin. A conical reflector is spaced distally of the distal end of the fiber alignment grooves and the fibers therewithin. A ball tip may be fused onto the distal end of the delivery fibers and/or the return fibers needed with the alignment grooves of the housing of this probe. The ball tips provide an enlarged variation of beam spread for the light energy being delivered or returned through their respective fibers. The central lumen within the extrusion may carry a guide wire for delivery of the probe within a body conduit, or the central lumen may also include one or more energy delivery fibers for delivering light signal energy to that probe location.

Yet another embodiment contemplates an elongated probe comprised of an elongated housing having a plurality of alignment grooves fabricated peripherally therein. The alignment grooves in this embodiment are arranged both adjacent the external peripheral surface of the housing carrying those signal fibers, and also alternatingly on the inner surface of the annularly shaped housing so as to thus permit a greater number of fibers or a greater fiber density to also permit alterations or changing in fiber spacing for greater control of fibers and their respective beams of light energy which they deliver or receive. The annular housing into which the alignment grooves are fabricated mates about an elongated extrusion having a central bore therethrough. An annular array of lensed prisms in this embodiment are arranged distally of the annular alignment groove housing. Each respective lensed prism in the annular array of multiple lensed prisms may function with and direct an energy signal to and from more than one adjacent signal fiber. Such an annular array of lensed prisms would permit overlapping light energy signals to be sent and/or received through adjacent signal fibers. Each of the fibers of course have their proximal ends in communication with an energy generating apparatus and an energy receiving and analysis apparatus for analysis of light signals that have been sent and reflected through various body tissues external of the catheter probe and received through the appropriate return fibers for computer analysis and reporting.

A still further embodiment of the probe of the present invention contemplates an elongated housing disposed about a central extrusion with a bore thereto. The elongated housing has a distalmost end which is situated adjacent the distal end of the extruded core. The elongated housing has a proximalmost half end portion with a plurality of parallel longitudinally directed alignment grooves therein. The alignment grooves in this embodiment have a distal end which define a reflective surface fabricated on the housing portion thereof. The respective reflective distalmost end portions of the alignment grooves are arranged at a different angle with respect to the longitudinal axes of the respective light signal fibers disposed within those alignment grooves. The reflective surfaces therefore, may preferably deliver a narrow beam of energy and may return (collect) a wide beam of energy reflected from the radially adjacent tissue within which the elongated probe is placed. This permits a more localized energy input and a larger collection area to gather a more available signal (photons). Thus there is a larger numerical aperture on alternating reflective surfaces and a smaller numerical aperture between those large ones.

Thus what has been disclosed is a unique elongated probe arrangeable within the distalmost end of a mammalian body tissue engaging catheter, which elongated probe carries a plurality of light energy delivery members such as optical fibers or optical wavewguides and light energy collecting members such as optical fibers or optical waveguides. The collector members (fibers/waveguides) are preferably arranged in annular array with a longitudinally spaced apart variation about a central extrusion for yet another embodiment thereof. The central extrusion may contain a bore or lumen for a further fiber or guidewire to facilitate entrance within a body lumen. The spectrum of energy delivered and received by the annular array of fibers may run from the ultrasound to the ultraviolet or beyond. The proximal end of these elongated energy bearing fibers are in communication with an energy delivery source and an energy receiving and analyzing computer to properly analyze and permit subsequent treatment of the tissue within the mammalian body.

The invention thus may comprise a catheter tip apparatus arranged in a catheter for the delivery and collection of an energy signal to permit analysis and/or treatment of body tissue by the energy signal. The apparatus comprises an elongated housing having a plurality of annularly disposed elongated grooves arranged thereon; and a flexible energy-bearing fiber arranged in each of the elongated grooves, each of the fibers having a proximal end in communication with an energy delivery source or a signal analysis center.

Each of the fibers have a distalmost end in communication with a beam redirecting member such as for example, a planar or curvilinear reflector of parabolic, convex, concave, or aspherical configuration, mirror, dielectric mirror, refractive index interface or diffractive optical element for directing energy-analysis light or light energy treatment of body tissue in which the catheter is disposed. The grooves may be disposed on an external surface of the housing. The grooves may be disposed on an internal surface of the housing. The distalmost end of the fibers have a reflective surface thereat. The distalmost end of the fibers may be directed toward a redirecting member such as an angled reflective surface. The housing preferably has a longitudinally directed bore arranged centrally therethrough. An energy bearing fiber may be arranged within the bore of the housing. An elongated guidewire may be arranged through the bore to permit the catheter tip apparatus to be directed within a body lumen. The energy bearing fiber disposed within the bore may be longitudinally displaceable within the bore. The fibers may be longitudinally displaceable within the grooves in the housing. Each of the grooves may have a ledge at a distal end thereof to provide an abutment to a fiber disposed within the grooves. The grooves in the housing may be dissimilar in axial length. The reflective surface may comprise an annular reflective surface. The annular reflective surface may be longitudinally displaceable with respect to the distal end of the grooves. Each of the reflective surfaces may be of equal arcuate width with respect to the width of each of the grooves. Each of the reflective surfaces may be of larger arcuate dimension than the arcuate dimension of each of the grooves. The reflective surface on at least one of said fibers may comprise a ball. The reflective surface may be arranged at an angle of about 45 degrees with respect to the longitudinal axis of the fiber. The housing may include a proximal portion of reduced diameter with respect to the housing containing the grooves. The redirecting members may thus be comprised an annular array of reflectors such as redirecting members such as identified hereinabove. At least one of the annular array of prisms may be in communication with at least two of the fibers. The reflective surface may comprise a conical reflector disposed circumferentially adjacent the grooves. The circumferentially adjacent reflective surfaces may be dissimilar to one another. The reflective surface may be of arcuate configuration in the longitudinal direction.

The present invention also comprises a catheter tip apparatus arranged in a catheter for the delivery and collection of a light energy signal to permit analysis and/or treatment of body tissue adjacent the catheter tip apparatus by the energy signal. The apparatus comprises an elongated housing having a longitudinal axis and a plurality of annularly disposed elongated grooves arranged thereon; and a flexible light energy-bearing member such as an optical fiber or waveguide (fibers cited for simplicity) arranged in each of the elongated grooves.

Each of the fibers have a proximal end in communication with a light energy delivery source or a light signal analysis center. Each of the fibers have a distal face in spaced-apart light transmissive communication with a reflector arrangement for directing illumination of body tissue for energy treatment of body tissue and analysis of the tissue in which the catheter is disposed. The fiber in each of the grooves may comprise an annular array of axially disposed light bearing fibers.

The reflector may comprise a single annular surface arranged distally adjacent the face end of each of the fibers. The reflector may comprise a discrete independent reflective surface arranged distally adjacent each face end of each of the fibers as an annular array of adjacent reflectors. The reflector may comprise a prism. The reflector may comprise an annular prism arranged distally adjacent the end face of each of the fibers. The adjacent reflectors in the annular array may have different surface characteristics. The adjacent reflectors in the annular array may be disposed at different angles with respect to the longitudinal axis of the housing. The adjacent fibers in the annular array of fibers may carry different light signals from one another. The housing may have a central lumen extending therethrough, and an elongated light signal fiber may be arranged therein. The fiber arranged in the central lumen may be longitudinally displaceable with respect to the probe of the elongated housing. Each of the independent reflective surfaces may be disposed at differing longitudinal locations with respect to the elongated housing. At least one of the annular array of fibers may have a ball tip thereon for dispersed light transmission. The reflector arrangement may be longitudinally displaceable with respect to the face ends of the light energy bearing fibers.

The invention may also comprise a catheter tip apparatus arranged in a catheter for the delivery and collection of a light energy signal to permit analysis and/or treatment of body tissue adjacent the catheter tip apparatus by the energy signal. The apparatus may comprise an elongated housing having a longitudinal axis and a plurality of annularly disposed elongated grooves arranged thereon; and a flexible light energy-bearing fiber arranged in each of the elongated grooves, each of the fibers having a proximal end in communication with a light energy delivery source or a light signal analysis center, each of the fibers having a distal face in spaced-apart light transmissive communication with the body tissue, the fiber in each of the grooves collectively comprising an annular array of axially disposed light bearing fibers. The light collecting fibers may each have a distal end which are longitudinally spaced apart from one another. Each of the light bearing fibers may be arranged to deliver and to collect light energy with respect to the body tissue being analyzed. Each of the light bearing fibers may have a light re-directing member in its light path. The light bearing fibers may collect a light energy beam which is wider than a light energy beam delivered to the body tissue,

BRIEF DESCRIPTION OF THE DRAWINGS

The objects and advantages of the present invention will become more apparent when viewed in conjunction with the following drawings in which.

DETAILED DESCRIPTION OF THE PREFERRED EMBODIMENTS

Figure 1A:
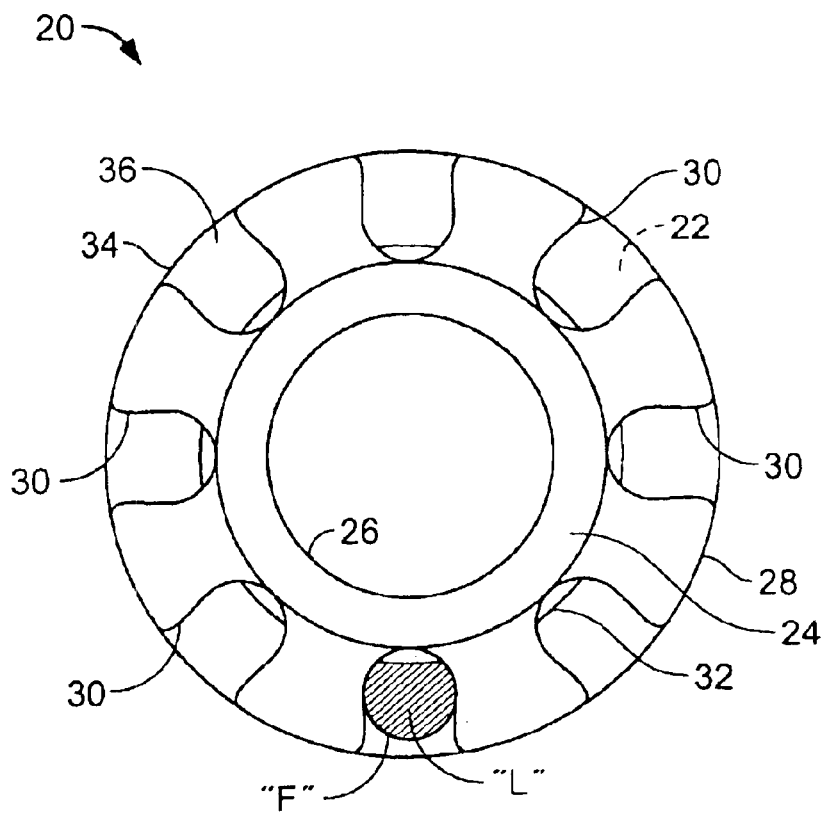
FIGS. 1(A), (B) and (C) are elevational views looking at the proximal end of an elongated housing of the present invention adapted to support a plurality of fibers.
Figure 1B:
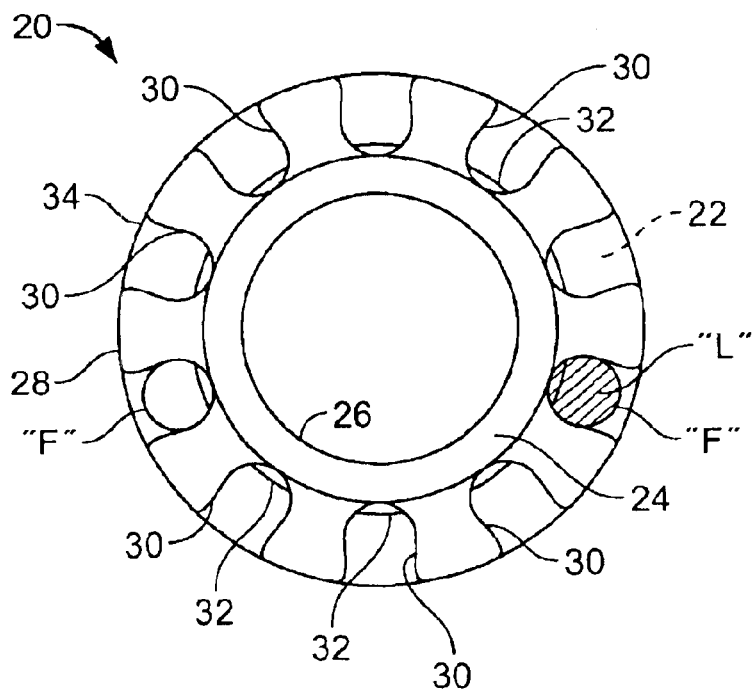
Figure 1C:
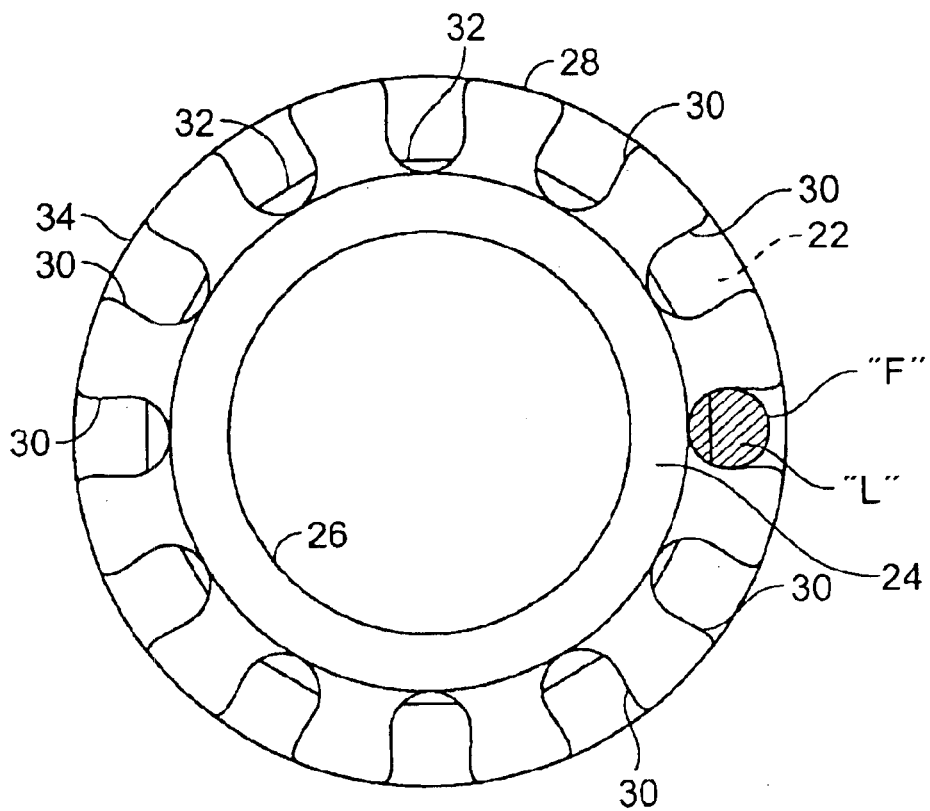

Referring now to the drawings in detail, and particularly to FIGS. 1(A), 1(B) and 1(C) there is shown in end views, the first preferred embodiments of the present invention which comprises an elongated generally cylindrically shaped housing 20 having a first or distal 22, and a second or proximal end 24. The housing 20 in a first preferred embodiments have a central bore 26 extending axially therethrough, which may be characterized as a lumen for receiving other elongated devices such as a guidewire or signal carrying members such as fibers or waveguides. The housing 20 has an outer peripheral surface 28 having a plurality of spaced apart, parallel, longitudinally directed alignment grooves 30 thereon, extending only axially along a central portion of the axial length of the housing 20. FIG. 1(A) discloses eight such grooves 30, FIG. 1(B) disclosing ten such grooves 30 and FIG. 1(C) disclosing twelve such fiber supporting grooves 30. A step-like ledge or shoulder 32 may be arranged transversely with respect to the longitudinal axis "L" of the alignment grooves 30 to act as an abutment or stop for each flexible light signal bearing fiber "F" disposed within the respective alignment grooves 30.

An enlarged annular flange 34 is disposed longitudinally adjacent the distalmost end of the alignment grooves 30 in this preferred embodiment, adjacent the distalmost end 22 of the probe housing 20. The flange 34 may have a sloped reflective surface 36 thereon for re-directing light energy rays from and to the light signal carrying fibers "F", as will be disclosed in further detail hereinbelow. The ledges or shoulders 32 arranged within the trough of the alignment grooves 30 may be aligned in a common radial plane or aligned in a number of parallel, spaced apart, radially directed planes, with respect to the longitudinal axis of the housing 20, as will also be disclosed hereinbelow. The ledges or shoulders 32 may be of varying radial heights, as shown in FIG. 1(C) in order to adjust to certain fiber "F" dimensions, and may be angled so as to effect slight radial displacement of the tips of each fiber "F" from the radially inner surface of the respective annular groove 30 in which it is disposed.

Figure 2:
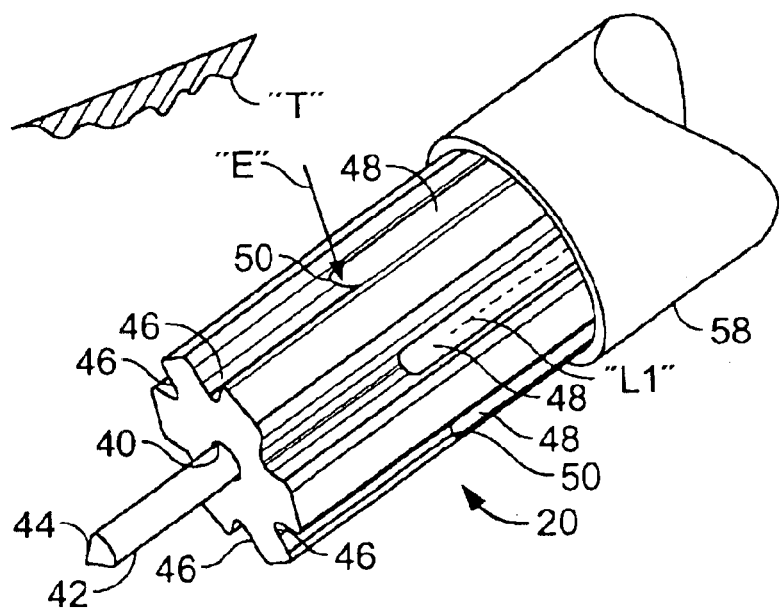
FIG. 2 is a perspective view of the distal end of an elongated probe having a central delivery fiber and a plurality of return fibers spaced longitudinally therearound.

A further embodiment of the generally cylindrically shaped housing 20 comprising the elongated probe is shown in FIG. 2, which housing 20 includes a central bore or lumen 40 through which a light signal delivery fiber 42 may be stationarily positioned or alternatively, it may be longitudinally adjustably disposed. The delivery fiber 42 would preferably have a polished conical tip 44 on its distalmost end. The elongated housing 20 in this embodiment would have the plurality of parallel longitudinally directed alignment grooves 46 circumferentially spaced apart about its periphery, each of the alignment grooves 46 having a longitudinally adjustable return light signal bearing fiber 48 disposed therein. Each of the return fibers 48 would have a polished face 50 arranged at an angle with respect to its own longitudinal axis "L1". The polished face 50 would function as a reflective surface for incoming energy rays "E" to be reflected in a return path longitudinally within the return fibers 42 from a tissue "T". The probe or elongated housing 20 may be longitudinally displaceable within an outermost catheter sheath 52, which sheath 52 would be advanced within a mammalian body for analysis and/or treatment by light energy waves with a proper analysis and/or treatment source, not shown for simplicity of the figures.

Figure 3:
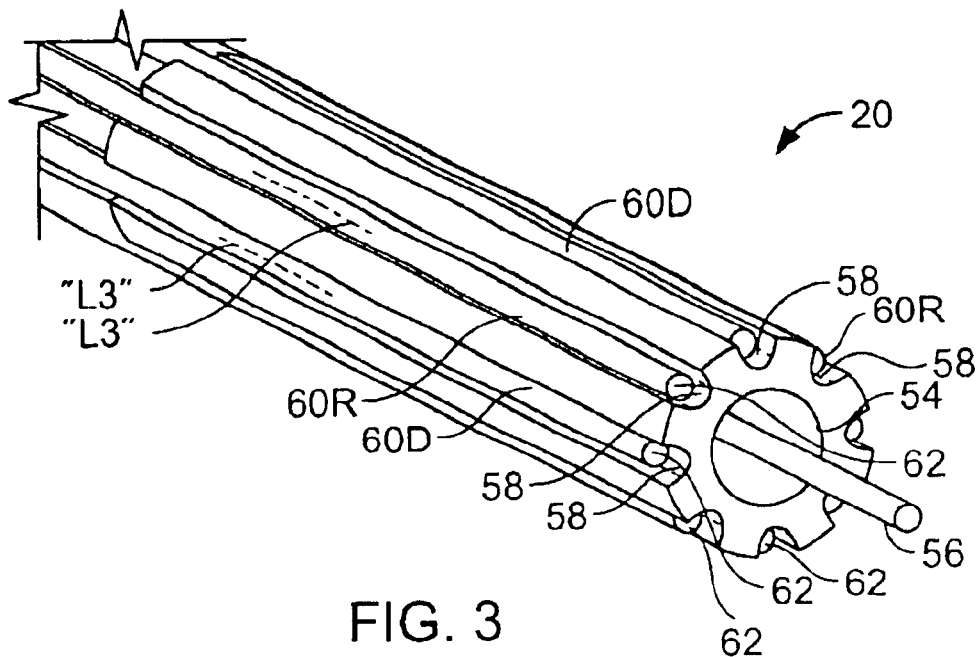
FIG. 3 is a perspective view of a further embodiment of the present invention showing an elongated probe having a central lumen and a plurality of alignment grooves spaced therearound.

A further embodiment of the present invention is shown in FIG. 3, which contemplates a generally cylindrically shaped housing 20 having a central bore 54 which functions as a lumen for a guide wire or further energy bearing fiber 56. The outer surface of the elongated probe or housing 20 has the aforementioned plurality of elongated, circumferentially disposed alignment channels or grooves 58 fabricated (as by extrusion, molding or machining) therein, with each of the elongated grooves 58 having a light bearing fiber 60 therein. Alternating circumferentially arranged light bearing fibers 60 in this embodiment may be a light delivery fiber 60D and a collection or return signal fiber 60R. The delivery signal fibers 60D and the return signal fibers 60R may each have a polished distalmost end face 62 thereon at an angle of about 45 degrees with respect to its longitudinal axis "L3" thereof. It is further contemplated that each individual light delivery or light return signal fiber 60D or 60R may be longitudinally displaceable within their respective alignment grooves 58 for adjustment of the desired analysis and/or treatment to mammalian body tissue being treated.

Figure 4A:
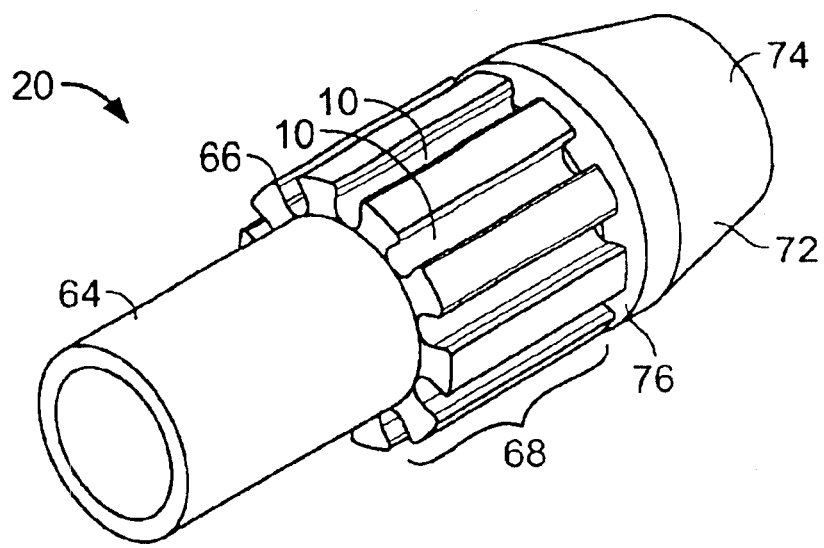
FIG. 4A is a perspective view of an elongated probe with a central bore therethrough and a segment of fiber alignment grooves spaced adjacent a conical distalmost end of the probe.
Figure 4B:
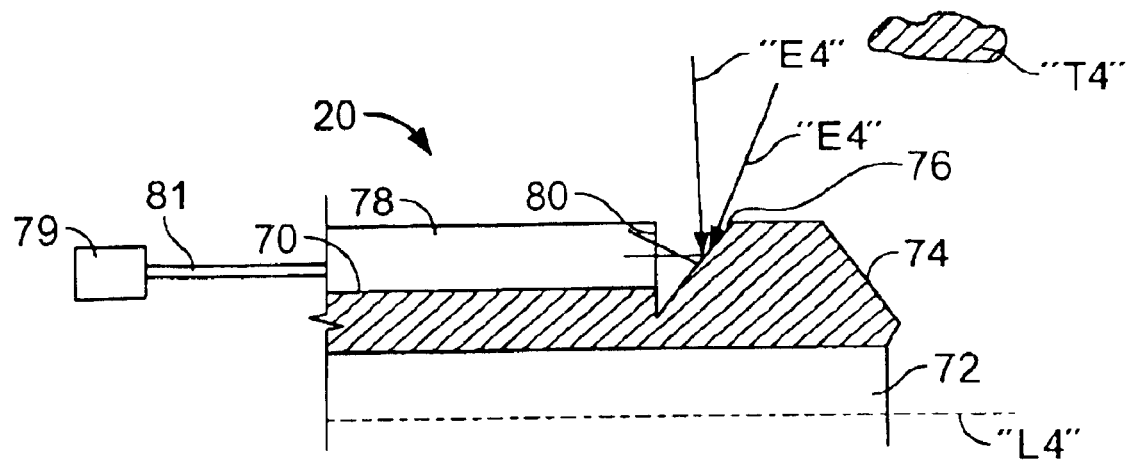
FIG. 4B is a sectional view of the housing shown in FIG. 4A.
Figure 4C:
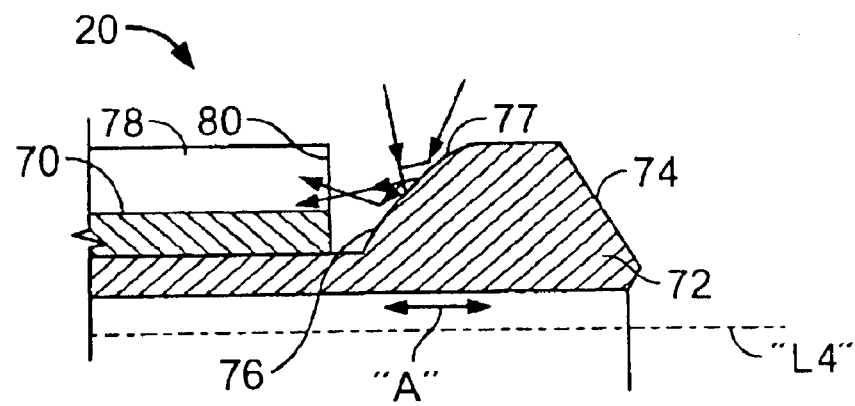
FIG. 4C is a view similar to 4B in a further embodiment thereof.

FIGS. 4(A), 4(B) and 4(C) present another preferred embodiment of the present invention which contemplates the elongated generally cylindrically shaped housing probe 20 having a proximal portion 64 of reduced diameter with respect to the outer surface 66 of a central portion 68 of the housing probe 20, the central portion 68 having a plurality of generally parallel, circumferentially spaced-apart, light energy bearing fiber alignment grooves 70 arranged peripherally therearound, and the housing probe 20 also having a distalmost nose portion 72. The distalmost nose portion 72 preferably has a sloped or tapered forward end 74 and an inclined or tapered rearward edge 76. The tapered rearward edge 76, of angular configuration as may be seen in FIG. 4(B), is a reflective surface. A light signal carrying fiber 78 would be arranged within each of the alignment grooves 70 as may be seen in FIG. 4(B). The signal fibers 78 have a distalmost end face 80 through which light energy signals "E4" would be delivered and/or received by bouncing off of the reflective angular surface on the tapered rearward edge 76 of the nose portion 72 of the elongated housing 20. The energy "E4" may be delivered from and/or returned to a proper energy generator and analysis apparatus 79, through a proper circuit 81, which provides a source and analysis of energy signals for analysis/ diagnosis and treatment of mammalian tissue "T4", exemplary for all the embodiments of the present invention. The nose portion 72 of the elongated housing 20 distal of the alignment grooves 70, may also be longitudinally displaceable as shown by arrow "A" along the longitudinal axis "L4" of the elongated housing 20. The rearward edge 76 may consist of a reflective surface 77 which may be somewhat arcuate or segmented in cross section or have angled reflective portions thereon, as represented in FIG. 4(C), thus to effect change therein by angular displacement of energy signals "E4" being delivered to or received from tissue adjacent to the elongated probe housing 20 in the distal end of a catheter in which the tissue analysis/treatment is being undertaken during the longitudinal adjustment of the nose portion 72.

Figure 5A:
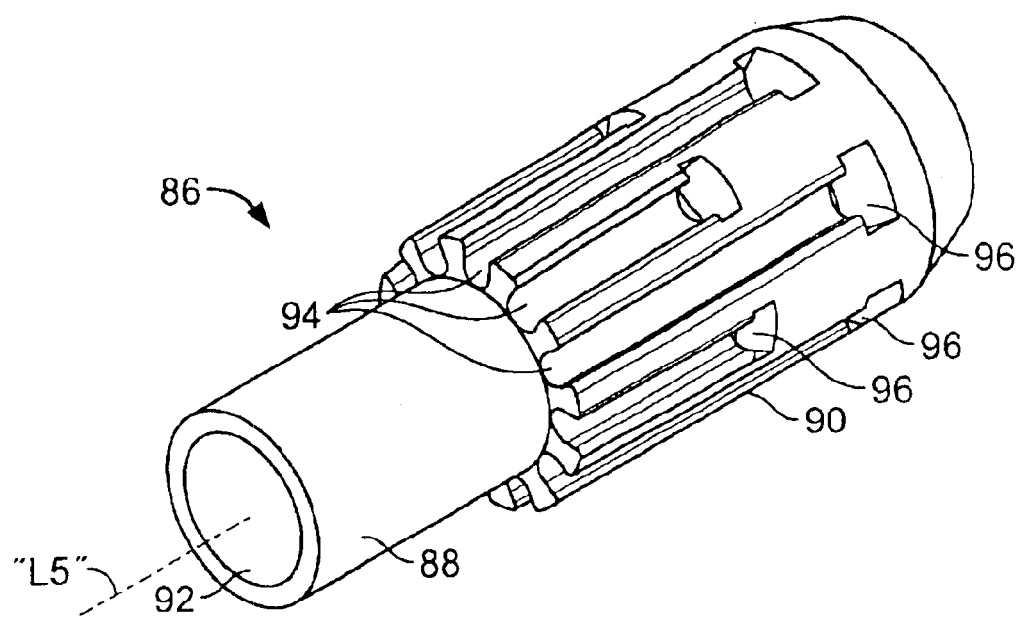
FIG. 5A is a perspective view of an elongated probe with alignment grooves therein.
Figure 5B:
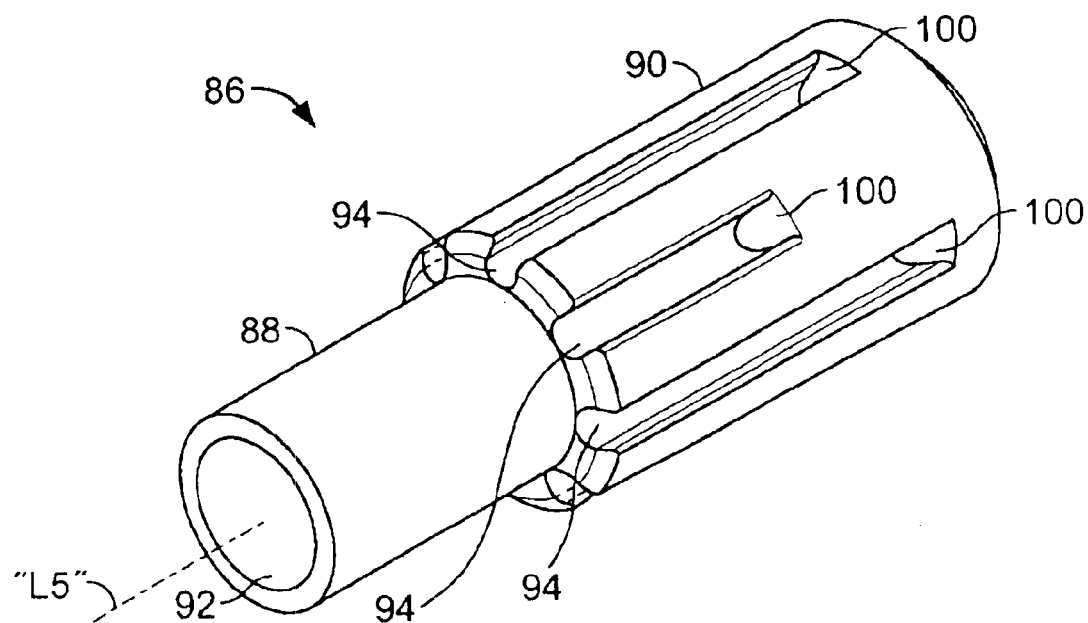
FIG. 5B is a view similar to FIG. 5A in a different embodiment thereof.

FIGS. 5(A) and 5(B) shown further embodiments of the present invention which contemplates an elongated generally cylindrically shaped housing 86 having a proximalmost end 88 of reduced diameter compared with the distal half 90 of the housing 86. A central bore 92 extends through the elongated housing 86 and out the distalmost end thereof 90. The distalmost half portion 90 of the elongated housing 86 has a plurality of generally parallel, spaced apart circumferentially disposed alignment grooves 94 fabricated therein. The alignment grooves 94 are parallel with respect to the longitudinal axis "L5" of the elongated housing 86. In this embodiment, the axial length of the respective alignment grooves 94 are dissimilar, as is shown in FIGS. 5(A) and 5(B). There is a longitudinal separation between the distalmost ends of alternate alignment grooves 94 to permit a spread in the collection and/or delivery of energy with respect to any fibers (not shown in these figures) disposed therewithin. The distalmost end of each alignment groove 94 in the elongated housing 86 of this embodiment has an angled polished mirror face 96 therein. The arcuate segment defining the mirror face 96 for each alignment groove is preferably arcuately (circumferentially) larger than the arcuate (circumferential) width of each respective alignment groove 94, as shown in FIG. 5(A). Such longitudinal difference between adjacent signal carrying fibers as represented by the longitudinal difference in the axial lengths of the grooves 94 fibers permits greater paths of analyses of body tissue being examined or treated.

Another embodiment which is generally similar to the aforementioned embodiment, contemplates mirrors 100 on the distal end of the alignment grooves 94 being the same arcuate (width) dimension as the respective alignment grooves 94 in which they sit, as is shown in FIG. 5(B).

Figure 6:
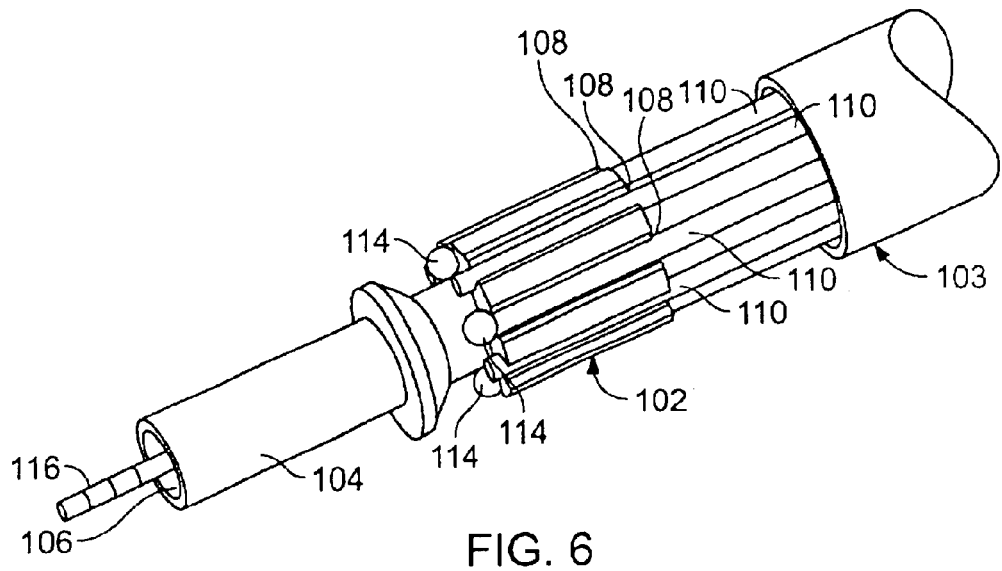
FIG. 6 is a perspective view of an extruded central lumen for an elongated probe with alignment grooves and light signal fibers in a further embodiment thereof.

FIG. 6 shows yet another embodiment contemplated for the elongated probe housing 102 for the distal end of a catheter 103 which may comprise a single elongated extrusion 104 having a bore 106 extending longitudinally therethrough. The extrusion's distal end defines the probe component 102 in this example. The housing probe 102 in this component also includes a plurality of axially aligned alignment grooves 108 exterior to the extrusion 104, the alignment grooves 108 each carrying a fiber 110 spaced therewithin. A conical reflector 112 is spaced distal of the distal end of the fiber alignment grooves 108 and the fibers 110 therewithin. A ball tip 114 may be fused onto the distal end of the delivery fibers 110 and/or the return fibers 110 seated within the alignment grooves 108 of the housing 102 of this probe 102. The ball tips 114 preferably provide a lens arrangement or alternatively a reflective arrangement for an enlarged variation of beam spread for light energy being delivered or returned through their respective fibers 110. The central lumen 106 within the extrusion 104 may carry a guide wire 116 for delivery of the probe 102 within a body conduit, or the central lumen 106 may also include one or more energy delivery fibers, not shown for clarity, for delivering light signal energy to that probe location.

Figure 7:
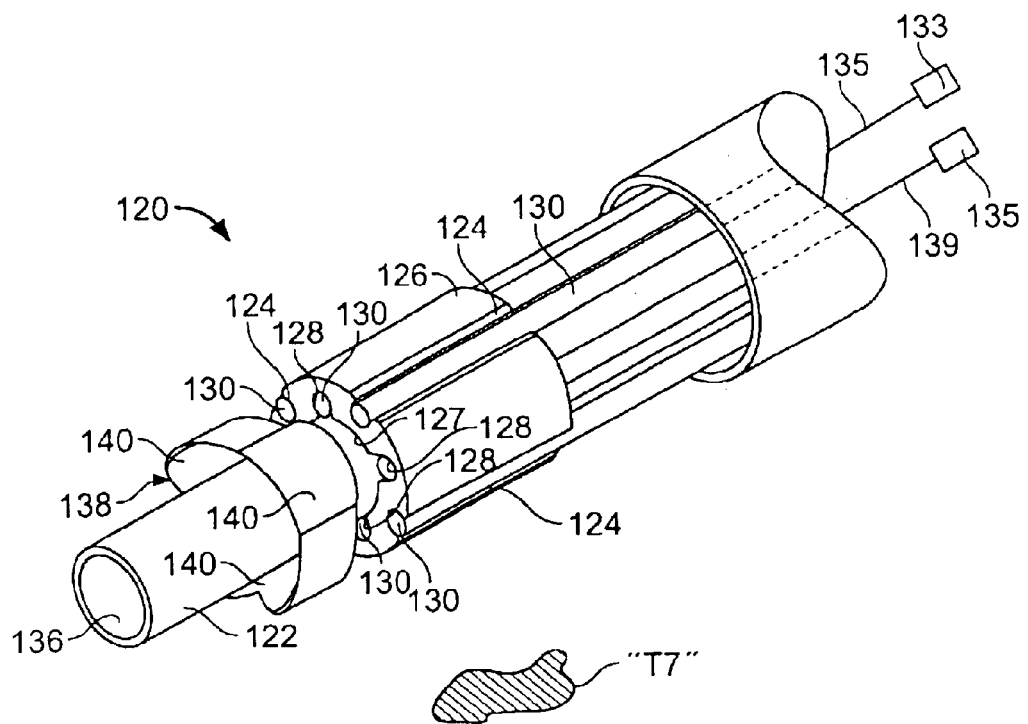
FIG. 7 is a view similar to FIG. 6 with an alignment groove arrangement in a different embodiment thereof.

FIG. 7 shows yet another preferred embodiment of the present invention which contemplates an elongated probe 120 comprised of an extruded elongated housing 122 having a plurality of external and internal alignment grooves 124 and 128 fabricated peripherally and circumferentially therein. The alignment grooves 124 in this embodiment are arranged both adjacent the external peripheral surface 126 of the housing 122 each carrying a signal fiber 130, and also alternatively on the inner surface 127 of the annularly shaped housing 122 so as to permit a greater number of fibers 130 or a greater fiber density to permit alterations or changing in fiber spacing for greater control of fibers 130 and their respective beams of light energy which they deliver or receive. The annular housing 122 into which the alignment grooves 124 and 128 are fabricated mates about the elongated extrusion 122 having a central bore 136 therethrough. An annular array of lensed prisms 138 in this embodiment are arranged distally of the annular alignment groove housing 120. Each respective lensed prism 140 in the annular array of multiple lensed prisms 138 may function with and direct an energy signal to and from more than one adjacent signal fiber 130. Such an annular array of lensed prisms 138 would permit overlapping energy signals to be sent and/or received through adjacent signal fibers 130. Each of the fibers 130 have their proximal ends in communication through a proper circuit 135 with an energy generating apparatus 133 and an energy receiving and analysis apparatus 137 in communication through a proper circuit 139, for analysis of light energy signals that have been sent and reflected through various body tissues "T7" external of the catheter probe 120 and received through the appropriate return fibers for computer analysis and reporting.

Figure 8A:
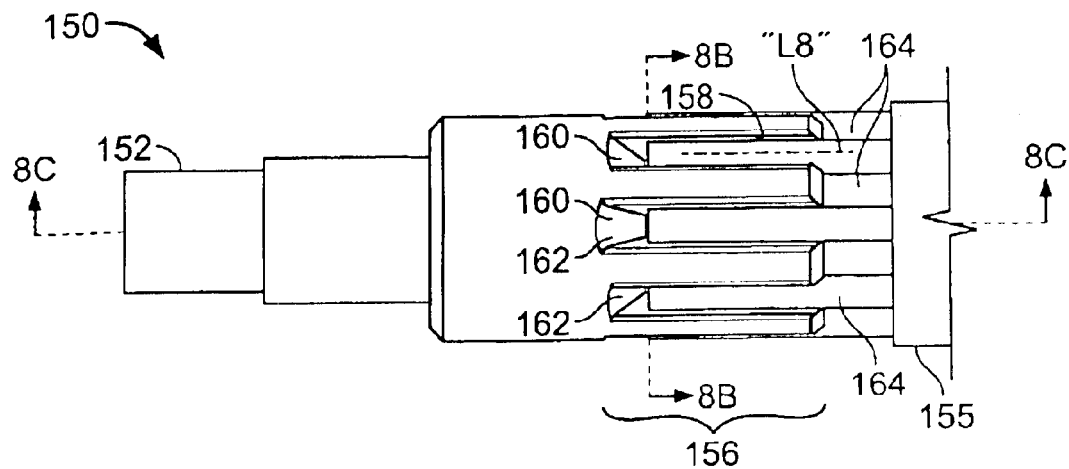
FIG. 8A is a side elevational view of the distal end of an elongated probe with alignment grooves therein in a yet further embodiment thereof.
Figure 8B:
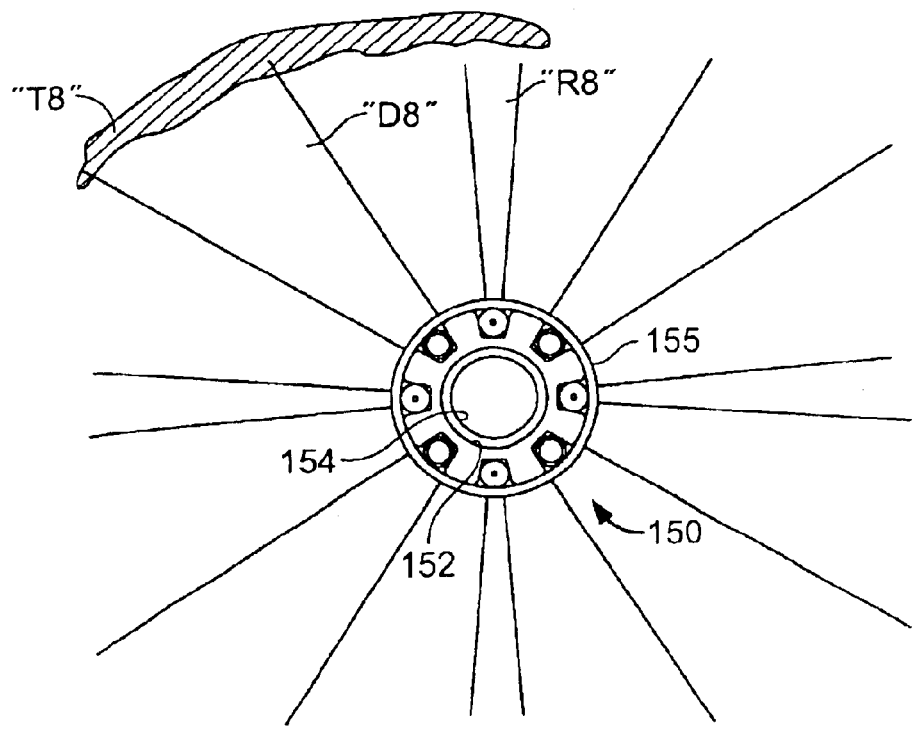
FIG. 8B is a view taken along the lines 8B—8B from FIG. 8A.
Figure 8C:
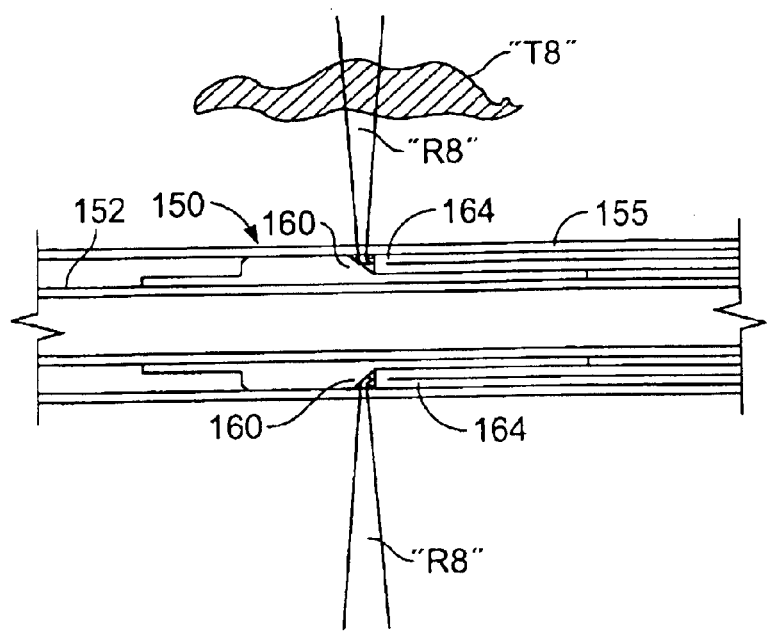
FIG. 8C is a view taken along the lines 8C—8C of FIG. 8A.
Figure 8D:
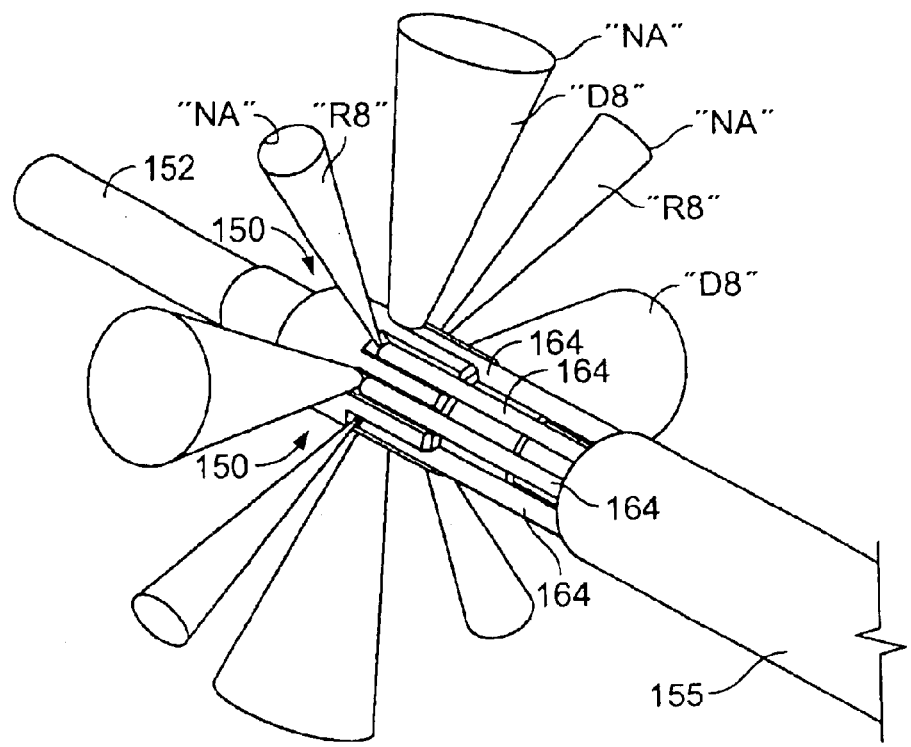
FIG. 8D is a perspective view of the elongated probe showing representations of the light energy signals emitted and received therefrom.

A still further preferred embodiment of the probe of the present invention is shown in FIGS. 8(A), 8(13), 8(C) and 8(D) which embodiment contemplates an elongated housing 150 disposed about a central extrusion 152 having an inner bore 154 therewith, and placed in an energy beam transparent catheter sheath 155. The elongated housing 150 has a distalmost end which is situated adjacent the distal end of the extruded core 152. The elongated housing 150 has a proximalmost half end portion 156 with a plurality of parallel, longitudinally directed, circumferentially disposed alignment grooves 158 therein. The alignment grooves 158 in this embodiment have a distal end 160 which define a reflective surface 162 fabricated on the housing portion 156 thereof. The respective reflective distalmost end portions 160 of the alignment grooves 158 are arranged at a different angle with respect to the longitudinal axes "L8" of the respective signal fibers 164 disposed within those alignment grooves 158. The reflective surfaces 162, therefore, may deliver a wider beam of light energy "D8" and may return a narrower beam of light energy "R8" reflected from the radially adjacent tissue "T8" within which the elongated probe is placed, as represented in FIGS. 8(B), 8(C) and 8(D). Thus there is a larger numerical aperture "NA" on alternating reflective surfaces and a smaller numerical "NA" aperture between those large ones. The delivery numerical aperture NA may range between NA=0.1 to NA=0.6, while the collection numerical aperture NA may range between NA=0.1 to NA=0.7. Beam redirecting members such as mirrors, lenses, dielectric mirrors, diffractive optical elements may have a separation of about 0.1 mm to about 2 mm.

Thus what has been disclosed is a unique elongated probe arrangeable within the distalmost end of a mammalian body tissue engaging catheter, which elongated probe carries a plurality of energy delivery members such as for example optical fibers or optical waveguides and energy collecting members such as optical fibers or optical waveguides or the like. The collector members (fibers etc) are preferably arranged in annular array about a central extrusion. The central extrusion may contain a bore or lumen for a further fiber or guidewire to facilitate entrance within a body lumen. The spectrum of energy delivered and received by the annular array of fibers may run from the ultrasound to the ultraviolet or beyond. The proximal end of these elongated energy bearing fibers are in communication of course, with an energy delivery source and an energy receiving and analyzing computer to properly analyze and permit subsequent treatment of the tissue within the mammalian body. Delivery of light energy may be made from a single fiber and collected from a plurality of spaced apart collectors or may be delivered by a plurality of fibers and collected by a single collection fiber. Alternatively, in a further embodiment, each light bearing member such as a fiber may function as both a light delivery member (fiber etc) and a light collection member (fiber etc).

I claim:

1. A catheter tip apparatus arranged in a catheter for the delivery and collection of an energy signal to permit energy signal analysis and/or energy signal treatment of body tissue by said energy signal, said apparatus comprising:
an elongated housing having a plurality of annularly disposed elongated open grooves arranged thereon; and
a flexible energy-bearing member arranged in each of said elongated open grooves, each of said energy-bearing members having a proximal end in communication with an energy delivery source or a signal analysis center, each of said energy-bearing members having a distalmost end in communication with a beam redirector member for directing energy between said energy-bearing members and body tissue in which said catheter is disposed.

2. The catheter tip apparatus as recited in claim 1, wherein said grooves are disposed on an external surface of said housing.

3. The catheter tip apparatus as recited in claim 1, wherein said grooves are disposed on an internal surface of said housing.

4. The catheter tip apparatus as recited in claim 1, wherein said distalmost ends of said energy-being members comprise an optical fiber with a beam redirecting arrangement thereat.

5. The catheter tip apparatus as recited in claim 4, wherein said beam-redirecting member comprises an annular reflective surface.

6. The catheter tip apparatus as recited in claim 5, wherein said annular reflective surface is longitudinally displaceable with respect to a distal end of said grooves.

7. The catheter tip apparatus as recited in claim 5, wherein each of said reflective surfaces are of equal arcuate width with respect to a width of each of said grooves.

8. The catheter tip apparatus as recited in claim 5, wherein each of said reflective surfaces is of larger arcuate dimension than the arcuate dimension of each of said grooves.

9. The catheter tip apparatus as recited in claim 4, wherein said beam redirecting member on at least one of said fibers comprises a ball.

10. The catheter tip apparatus as recited in claim 4, wherein said reflective surface is arranged at an angle of about 45 degrees with respect to a longitudinal axis of said fiber.

11. The catheter tip apparatus as recited in claim 4, wherein said reflective surface comprises an annular array of lensed prisms.

12. The catheter tip apparatus as recited in claim 11, wherein at least one of said annular array of prisms is in communication with at least two of said fibers.

13. The catheter tip apparatus as recited in claim 5, wherein said reflective surface comprises a conical reflector disposed circumferentially adjacent to said grooves.

14. The catheter tip apparatus as recited in claim 5, wherein circumferentially adjacent reflective surfaces are dissimilar to one another.

15. The catheter tip apparatus as recited in claim 5, wherein said reflective surface is of arcuate configuration in the longitudinal direction.

16. The catheter tip apparatus as recited in claim 1, wherein said distalmost ends of said energy bearing members are directed toward an angled reflective surface.

17. The catheter tip apparatus as recited in claim 1, wherein said housing has a longitudinally directed bore arranged centrally therethrough.

18. The catheter tip apparatus as recited in claim 17, including an energy-bearing member arranged within said bore of said housing.

19. The catheter tip apparatus as recited in claim 17, including an elongated guidewire arranged through said bore to permit said catheter tip apparatus to be directed within a body lumen.

20. The catheter tip apparatus as recited in claim 18, wherein said energy bearing member comprises a fiber disposed within said bore, said fiber being longitudinally displaceable within said bore.

21. The catheter tip apparatus as recited in claim 1, wherein said energy bearing members comprises optical fibers, said fibers being longitudinally displaceable within said grooves in said housing.

22. The catheter tip apparatus as recited in claim 1, wherein each of said grooves has ledge at a distal end thereof to provide an abutment to an energy-bearing member disposed within said grooves.

23. The catheter tip apparatus as recited in claim 1, wherein said grooves in said housing are dissimilar in axial length.

24. The catheter tip apparatus as recited in claim 1, wherein said housing includes a proximal portion of reduced diameter with respect to a portion of said housing containing said grooves.

25. A catheter tip apparatus arranged in a catheter for the delivery and collection of a light energy signal to permit analysis and/or treatment of body tissue adjacent to said catheter tip apparatus by said energy signal, said apparatus comprising:
an elongated housing having a longitudinal axis and a plurality of annularly disposed elongated open grooves arranged thereon; and
a flexible light energy-bearing fiber arranged in each of said elongated open grooves, each of said fibers having a proximal end in communication with a light-energy delivery source or a light-signal analysis center, each of said fibers having a distal face in spaced-apart light transmissive communication with a reflector arrangement for directing energy between said fibers and body tissue in which said catheter is disposed, said fibers in each of said grooves being arranged as an annular array of axially disposed fibers.

26. The catheter tip apparatus as recited in claim 25, wherein said reflector comprises a single annular surface arranged distally adjacent to a face end of each of said fibers.

27. The catheter tip apparatus as recited in claim 25, wherein said reflector comprises a discrete independent reflective surface arranged distally adjacent to face ends of each of said fibers, said reflective surfaces being arranged as an annular array of adjacent reflectors.

28. The catheter tip apparatus as recited in claim 27, wherein adjacent reflectors in said annular array have different surface characteristics.

29. The catheter tip apparatus as recited in claim 27, wherein adjacent reflectors in said annular array are disposed at different angles with respect to said longitudinal axis of said housing.

30. The catheter tip apparatus as recited in claim 27, wherein said independent reflective surfaces are disposed at differing longitudinal locations with respect to said elongated housing.

31. The catheter tip apparatus as recited in claim 25, wherein said reflector arrangement comprises a lensed prism.

32. The catheter tip apparatus as recited in claim 25, wherein said reflector arrangement comprises an annular lensed prism arranged distally adjacent to said end face of each of said fibers.

33. The catheter tip apparatus as recited in claim 25, wherein adjacent fibers in said annular array of fibers carry different light signals from one another.

34. The catheter tip apparatus as recited in claim 25, wherein said housing has walls forming a central lumen extending therethrough, and an elongated light-signal fiber passes through the central lumen.

35. The catheter tip apparatus as recited in claim 34, wherein said elongated light-signal fiber is longitudinally displaceable with respect to a probe of said elongated housing.

36. The catheter tip apparatus as recited in claim 25, wherein at least one fiber from said annular array of fibers has a ball tip thereon for dispersed light transmission.

37. The catheter tip apparatus as recited in claim 25, wherein said reflector arrangement is longitudinally displaceable with respect to face ends of said light energy-bearing fibers.

38. A catheter tip apparatus arranged in a catheter for the delivery and collection of a light energy signal to permit analysis and/or treatment of body tissue adjacent to said catheter tip apparatus by said energy signal, said apparatus comprising:
   an elongated housing having a longitudinal axis and a plurality of annularly disposed elongated open grooves arranged thereon; and
   a flexible light energy-bearing fiber arranged in each of said elongated open grooves, each of said fibers having a proximal end in communication with a light energy-delivery source or a light-signal analysis center, each of said fibers having a distal face in spaced-apart light transmissive communication with said body tissue, said fiber in each of said grooves being arranged as an annular array of axially disposed fibers.

39. The catheter tip apparatus as recited in claim 38, wherein said fibers have distal ends that are longitudinally spaced apart from one another.

40. The catheter tip apparatus as recited in claim 38, wherein each of said fibers are arranged to deliver and to collect light energy with respect to said tissue being analyzed.

41. The catheter tip apparatus as recited in claim 38, wherein each of said fibers has a light re-directing member in its light path.

42. The catheter tip apparatus as recited in claim 38, wherein said fibers collect a light energy beam that is wider than a light energy beam delivered to said body tissue.

43. The catheter tip arrangement as recited in claim 41, wherein said light redirecting member has a configuration selected from the group consisting of convex, concave, aspherical, planar, and parabolic.

* * * * *